United States Patent
Der Ovanesian

Patent Number: 6,083,256
Date of Patent: *Jul. 4, 2000

[54] NNT OR COLD PAD WITH INNER ELEMENT

[76] Inventor: Mary Der Ovanesian, 6650 Coolidge St., Hollywood, Fla. 33024

[*] Notice: This patent is subject to a terminal disclaimer.

[21] Appl. No.: 09/118,488

[22] Filed: Jul. 17, 1998

Related U.S. Application Data

[63] Continuation-in-part of application No. 08/689,899, Aug. 15, 1996, and a continuation-in-part of application No. PCT/US98/01779, Jan. 30, 1998.

[51] Int. Cl.⁷ ........................................................... A61F 7/00
[52] U.S. Cl. ........................... 607/114; 607/96; 607/112; 62/530
[58] Field of Search .................. 607/96–114; 62/530; 120/204; 383/901; 105/46

[56] References Cited

U.S. PATENT DOCUMENTS

| | | |
|---|---|---|
| 1,927,751 | 9/1933 | Mensi . |
| 1,964,962 | 7/1934 | Rosenblum . |
| 2,602,302 | 7/1952 | Poux . |
| 2,769,308 | 11/1956 | Krasno . |
| 2,800,456 | 7/1957 | Shepherd . |
| 2,984,839 | 5/1961 | Conrad et al. . |
| 3,149,943 | 9/1964 | Amador . |
| 3,191,392 | 6/1965 | Donnelly . |
| 3,429,138 | 2/1969 | Goldmerstein . |
| 3,463,161 | 8/1969 | Andrassy . |
| 3,491,761 | 1/1970 | Baker . |
| 3,500,014 | 3/1970 | Longo . |
| 3,506,013 | 4/1970 | Zdenek . |
| 3,559,416 | 2/1971 | Cornwall . |
| 3,804,077 | 4/1974 | Williams . |
| 3,871,376 | 3/1975 | Kozak ................................... 128/275.1 |
| 3,874,504 | 4/1975 | Verakas ................................. 206/219 |
| 3,951,127 | 4/1976 | Watson et al. ........................ 126/206 |
| 3,977,202 | 8/1976 | Forusz et al. ............................... 62/4 |
| 4,077,390 | 3/1978 | Stanley et al. ........................ 126/263 |
| 4,311,022 | 1/1982 | Hall ........................................ 62/457 |
| 4,462,224 | 7/1984 | Dunshee et al. ....................... 62/530 |
| 4,573,447 | 3/1986 | Thrash et al. ......................... 126/263 |
| 4,708,812 | 11/1987 | Hatfield ...................................... 252/70 |
| 4,753,241 | 6/1988 | Brannigan et al. .................... 128/380 |
| 4,753,242 | 6/1988 | Saggers .................................. 128/380 |
| 4,756,311 | 7/1988 | Francis .................................. 128/403 |
| 4,780,117 | 10/1988 | Lahey et al. ................................ 62/4 |
| 4,856,651 | 8/1989 | Francis .................................. 206/219 |
| 4,872,442 | 10/1989 | Manker ................................. 126/263 |
| 4,880,953 | 11/1989 | Manker ............................... 219/10.55 |
| 4,886,063 | 12/1989 | Crews ................................... 128/403 |
| 4,908,166 | 3/1990 | Slayer ..................................... 264/22 |
| 4,910,978 | 3/1990 | Gordon et al. .......................... 62/530 |
| 4,925,603 | 5/1990 | Nambu ................................... 264/28 |
| 4,962,761 | 10/1990 | Golden ................................. 128/400 |
| 5,069,208 | 12/1991 | Noppel et al. ......................... 128/403 |
| 5,179,944 | 1/1993 | McSymytz ............................. 128/403 |
| 5,245,938 | 9/1993 | Frye ...................................... 112/441 |
| 5,339,796 | 8/1994 | Manker ................................. 126/263 |
| 5,395,399 | 3/1995 | Rosenwald ............................ 107/108 |
| 5,395,400 | 3/1995 | Stafford et al. ........................ 607/109 |
| 5,423,996 | 6/1995 | Slayer ..................................... 252/70 |
| 5,429,762 | 7/1995 | Kitahara et al. ......................... 252/70 |
| 5,456,852 | 10/1995 | Isiguro .................................... 252/70 |
| 5,486,206 | 1/1996 | Avery .................................... 607/104 |
| 5,534,020 | 7/1996 | Cheyney et al. ....................... 607/108 |
| 5,552,075 | 9/1996 | Slayer ..................................... 252/70 |
| 5,840,080 | 11/1998 | Der Ovanesian ..................... 607/114 |
| 5,843,145 | 12/1998 | Brink .................................... 607/114 |

Primary Examiner—Linda C. M. Dvorak
Assistant Examiner—David M. Ruddy
Attorney, Agent, or Firm—Brinkley, McNerney, Morgan, Solomon & Tatum LLP

[57] ABSTRACT

A flexible heat transfer device for heating or cooling a surface such as the skin has an envelope formed from two sheets. The envelope contains a high thermal capacity first material such as a freezing gel that is flexible when frozen for good surface contact, A pouch within the envelope contains a high thermal capacity second material that may have different physical properties than the first material. The pouch may be segmented, or there may be multiple pouches. The device is more versatile in its applications and provides for more prolonged heating and cooling, The pouch may be in two parts within a frangible partition that generates heat or cold when the partition is ruptured and the two parts mixed.

20 Claims, 3 Drawing Sheets

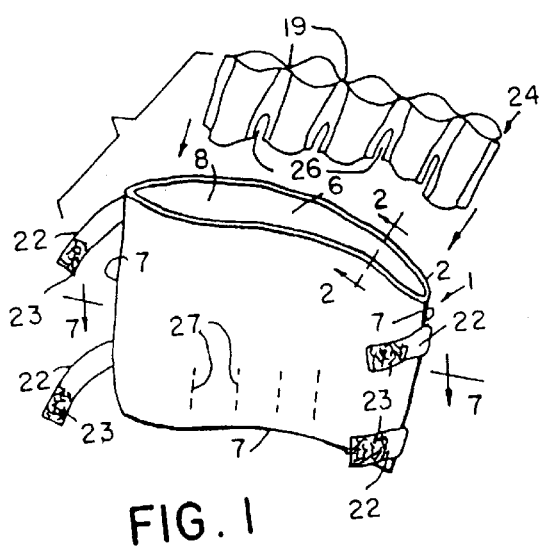
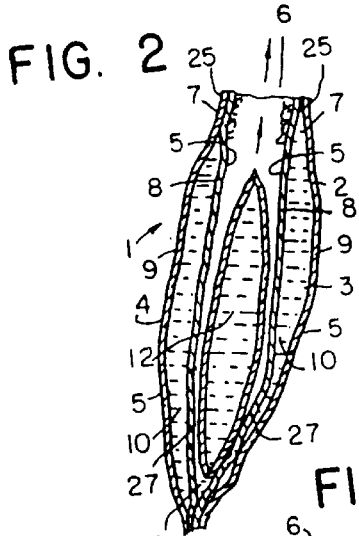
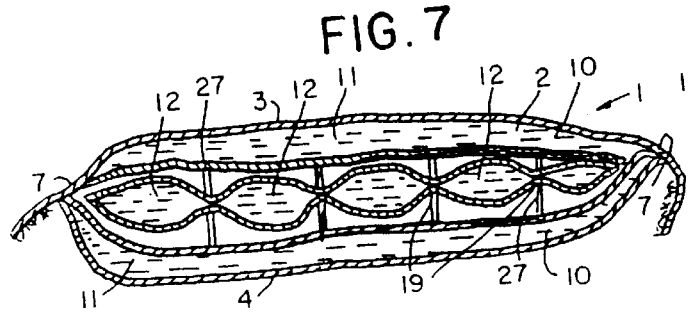
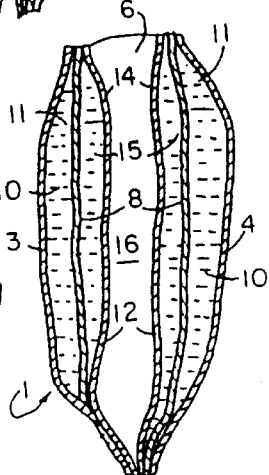
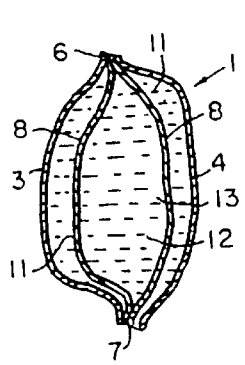
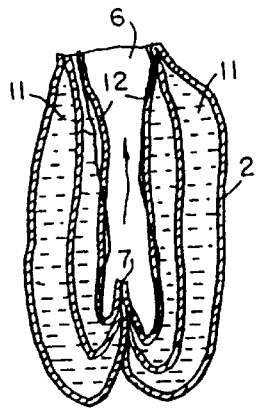
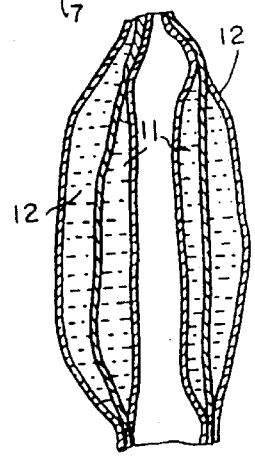

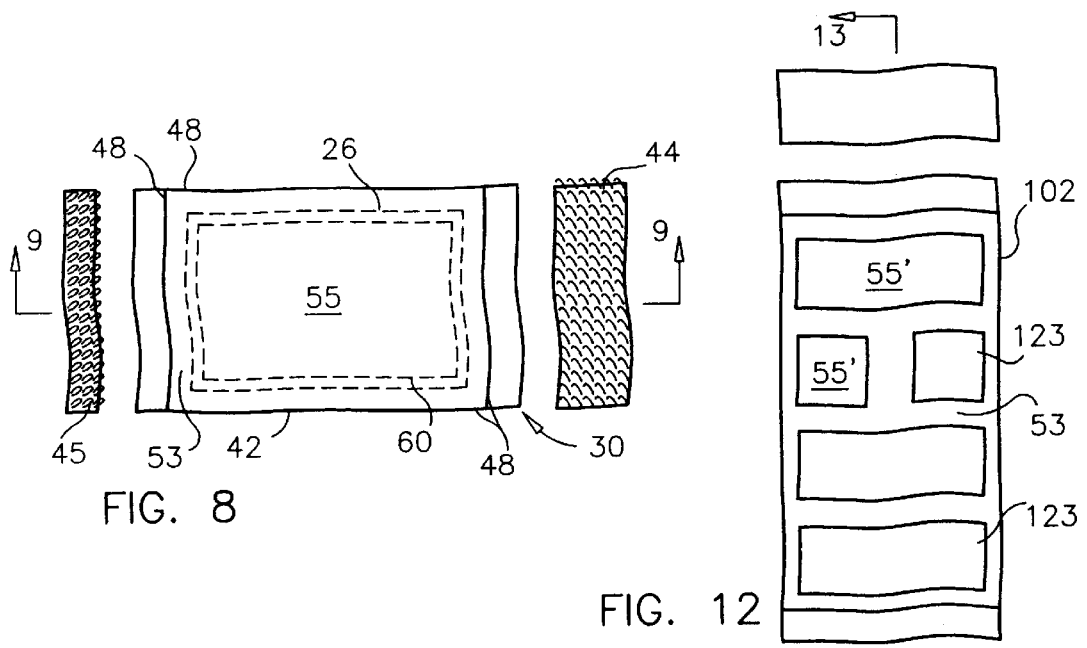
FIG. 8
FIG. 12
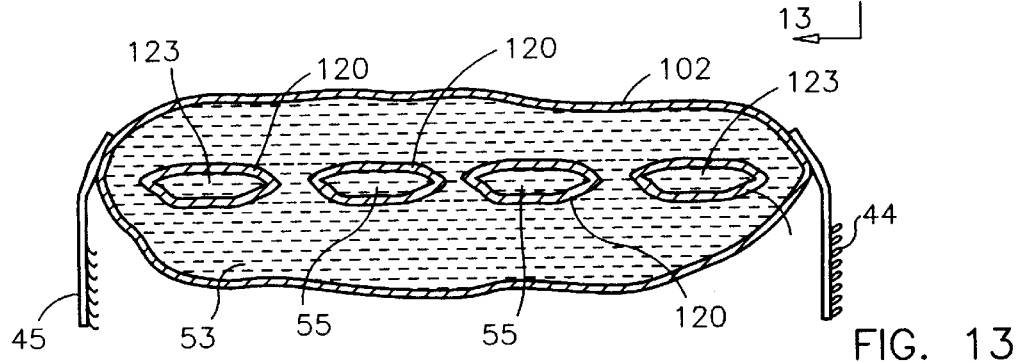
FIG. 13
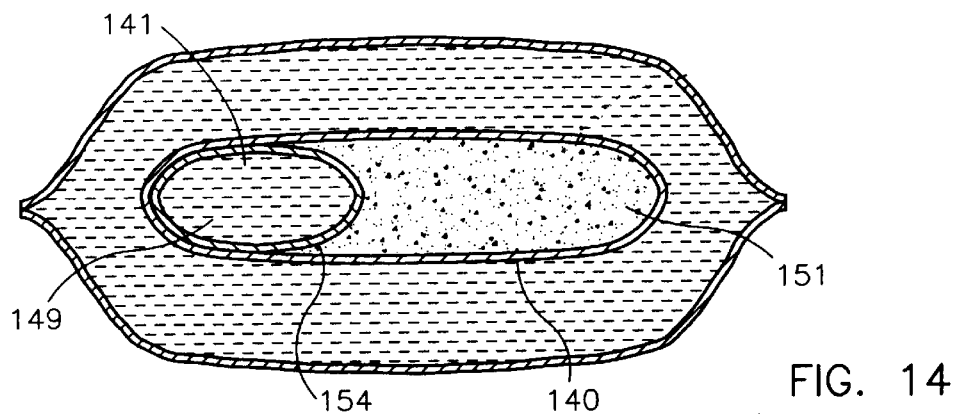
FIG. 14

NNT OR COLD PAD WITH INNER ELEMENT

CROSS-REFERENCE TO RELATED APPLICATIONS

This is a continuation in part of prior application Ser. No. 08/689,899, filed Aug. 15, 1996 and PCT Application Ser. No. PCT/US98/01779 filed Jan. 30, 1998.

STATEMENT REGARDING FEDERALLY SPONSORED RESEARCH OR DEVELOPMENT

N/A

BACKGROUND OF THE INVENTION

1. Field of the Invention

This invention relates to a reusable therapeutic device which may be used for cooling or heating and features a flexible bag which may be heated or cooled and then applied to a body part for thermal application with an inner element that enhances the thermal effects.

2. Description of Related Art

U.S. Pat. No. 4,592,358 issued Jun. 3, 1986 to Westplate provides a useful review of the patent literature in this art.

Despite the numerous advances that have been made in this art, people who need to apply heat or cold to the body for prolonged periods of time still find deficiencies in the available devices, because they don't provide relatively uniform temperature for relatively long periods of time, with the exception of the electric heating pads. When heat or cold is to be applied to the body surface, the temperature must not be so hot or cold as to be injurious or uncomfortable, while the total thermal capacity must be great enough to be therapeutically effective for a prolonged period of time.

BRIEF SUMMARY OF THE INVENTION

The invention comprises a flexible, conformable hot or cold pack having an envelope of a first high heat capacity material surrounding a second high heat capacity material for enhanced and more prolonged application of heating or cooling to any surface.

It is accordingly an object of the invention to provide a cooling and/or heating applicator that is sufficiently flexible to conform to various body parts to make surface contact for effective heat transfer.

It is another object that the applicator provide heating and/or cooling at an effective temperature for a greatly prolonged period of time for optimal therapeutic benefit.

It is another object that the device be reversible so that the surface properties may be altered in at least one alternative embodiment.

It is yet another object that the device have a removable inner portion that may be separately heated or cooled in an alternative embodiment of the invention.

Another object of the present invention is to provide a series of such hot or cold packs which are specifically designed to be conveniently and efficiently applied to parts of the anatomy such as the lumbar back region, the wrist, the knee or elbow, the cervical back region, i.e. the neck and upper back, the foot, the face, the leg, the pelvis, etc.

Yet another object of the present invention is to provide a hot or cold pack, or series of such hot or cold packs, which cause heat transfer with any body, animate or inanimate.

A still further object of this invention is to provide a hot or cold applicator for facilitating heat transfer with a body or body part in the form of such well known articles as gloves, socks, hoods, belts, or any other suitable clothing article.

It is also an object of this invention is to provide a hot or cold applicator which is combined with material for bandaging wounds.

It is also an object of this invention to provide a hot or cold applicator having an outer layer thereof at least a portion of which is capable of absorbing and holding liquid such as water to provide moist heat to a surface when the applicator is at an elevated temperature.

It is a further object of this invention to provide a hot or cold applicator having means thereon for connecting and/or holding such applicator to a surface to or from which heat is transferred from or to the applicator.

It is also an object of this invention to provide a hot or cold applicator for use in connection with forming or cooling articles of food and/or beverages.

These and other objects, advantages and features of the invention will become more apparent when the detailed description is studied in conjunction with the drawings, in which like elements are designated by the same reference characters in the various figures.

In accordance with these and other objects which will become apparent hereinafter, the instant invention will now be described with particular reference to the accompanying drawings.

BRIEF DESCRIPTION OF THE SEVERAL VIEWS OF THE DRAWINGS

FIG. 1 is a perspective view of the invention with a removable refrigerant pouch ready to be inserted.

FIG. 2 is a sectional view taken through line 2—2 of FIG. 1 with pouch inserted.

FIG. 3 is a sectional view, as in FIG. 2, of another embodiment of the invention with a non-removable inner high thermal capacity material.

FIG. 4 is a sectional view, as in FIG. 2, of another embodiment of the invention with reversible inner and outer high thermal capacity materials.

FIG. 5 is a sectional view of the embodiment of FIG. 4 partially everted.

FIG. 6 is a sectional view of the embodiment of FIG. 4 completely everted.

FIG. 7 is a sectional view taken through line 7—7 of FIG. 1.

FIG. 8 is a top plan view of another embodiment of the pad of the invention.

FIG. 12 is a top plan view of another embodiment of the invention.

FIG. 13 is a sectional view taken through line 13—13 of FIG. 12.

FIG. 14 is a sectional view of another embodiment of the invention.

DETAILED DESCRIPTION OF THE INVENTION

Figure 9:
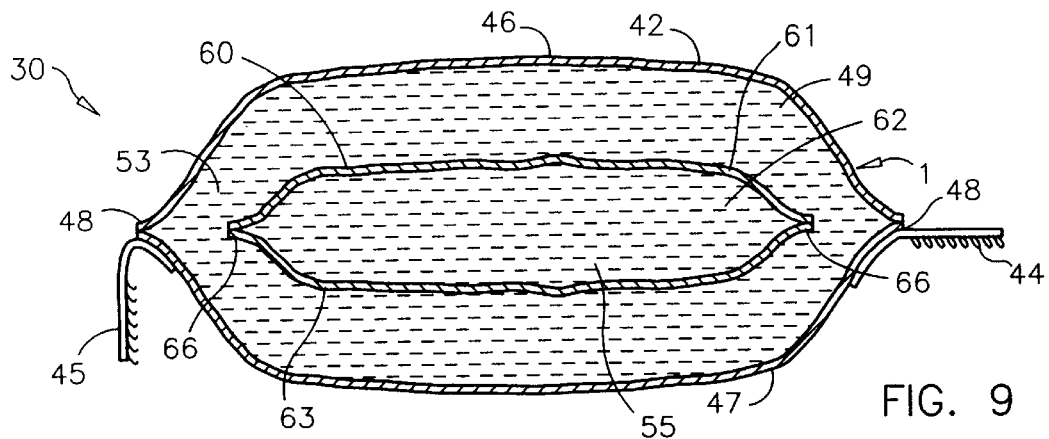
FIG. 9 is a sectional view taken through line 9—9 of FIG. 8.

Referring now first to FIGS. 1, 2 and 7, the embodiment of the invention shown here comprises a flexible heat transfer device 1 that conforms readily to the irregular surface of a body part so as to provide good surface contact for effective thermal transfer for heating or cooling. End straps 22 with hook and loop fasteners 23 permit the device to be wrapped around an arm, for example, and secured in place by the straps. The device 1 includes an outer envelope 2 formed of two double-walled sheets 3, 4 having broad faces 5. The sheets 3, 4 are joined together on 3 edges 7 and unjoined on one edge 6. Each double-walled sheet 3, 4 is formed of an inner panel a and an outerlpanel 9 sealed along all their edges 6, 7 to define therebetween a volume 10. The volumes 10 contain a first high thermal capacity material 11 such as one of the freezing gels well known in the art, such as that disclosed by U.S. Pat. No. 4,324,111 which changes state from liquid to slush at around zero degrees centigrade and requires considerable heat energy as it warms through this change of state to serve as an artificial ice that is not rigid. U.S. Pat. No. 5,314,005 discusses other materials for this purpose including some that may be heated in a microwave oven for use as hot packs.

The envelope so formed is open at the edge 6 to permit the insertion of a flexible pouch 24. The pouch 24 and the envelope are formed of thin flexible liquid-impermeable web such as plastic film. The thickness has been exaggerated for illustrative purposes.

The pouch 24 contains a second high thermal capacity material 12. After inserting the pouch 24 through the open side 6 of the envelope into the space 13 defined by the inner panels 8, the open side 6 may be closed by a releasable closure 25 which may be hook 25 and loop, snaps, zipper, or the like.

Multiple pouches 24 may be provided so that one is being used in the envelope while others are being chilled or heated.

The pouch 24 may be segmented as shown to make it more flexible and to maintain a flatter shape for insertion in the envelope by seams 19 sealing together the two flexible webs 14 that make up the outer wall of the pouch. The seams 19 may be provided with notches 26 that cooperate with short partitions 27 connecting the inner panels 8. This stabilizes the pouch within the envelope.

The high thermal capacity material 12 in the pouch may be identical to, or different from, the material 11 in the envelope walls. It may even be rigid when frozen such as plain water, since segmentation provides flexibility.

The materials 11 and 12 may be selected on the basis of their particular physical properties to enhance the utility of the device. Those properties include, but are not limited to, heat of fusion, heat capacity, thermal conductivity, temperature of transition from liquid to solid, rigidity in the solid phase, reaction to microwave radiation, vapor pressure and boiling point.

The term high thermal capacity material is used herein to refer to a material such as water, a freezing gel, or materials disclosed in the U.S. Pat. Nos. 5,314,005; 4,592,358; 4,324,111 (the disclosures of all three of which are incorporated herein by reference as though fully set forth herein) that have a high heat of fusion and/or a high heat capacity such that a relatively large number of calories is required to change the temperature thereof compared to most materials. The principal ingredient in most of these high thermal capacity materials is water. Its heat of fusion, that is the amount of heat given up when going from liquid to solid or absorbed when going from solid to liquid, is 80 calories per gram. This is more than triple that of most materials. The heat capacity of water, that is the amount of heat given up or absorbed to change its temperature 1 degree centigrade is 1 calorie per gram. This is more than triple that of most materials. A high thermal capacity material is one having a heat of fusion and/or a heat capacity that is at least one half that of water.

Water-containing high thermal capacity materials have been found to be particularly suitable tar use with hot and cold applicators such as those described herein because water has an excellent heat capacity and density. Consequently, by choosing the composition which undergoes a change of phase at a predetermined, desired temperature, enables the material to release or absorb a significant quantity of heat depending upon when the device is used as a hot or cold pad, respectively. Accordingly, the material chosen should be one that undergoes a phase change while being recharged such that it will also go through the reverse phase change at the desired temperature when being used to heat or cool a surface.

Insulation such as foam is comprised mostly of trapped air which has a low thermal conductivity, i.e. it transmits calories poorly. Because it is a gas, it has very low density (g/cc). Consequently it has very low thermal capacity per volume of insulation.

Thermal conductivity of the material 11 is important in the rate of transfer of heat to or from the insert or pouch 24. By acting as a partial insulator, it can prolong the cooling effect and also prevent a very cold or hot insert from injuring the skin, while maintaining a relatively uniform surface temperature. The envelope 2 may also be used without the pouch, as desired.

Referring now to FIG. 3, a heat transfer device 1 is shown in which the two double-walled sheets 3, 4 are sealed an all edges 6, 7 with a sealed inner space 13 defined by the two inner panels 8 containing the second high thermal capacity material 12 and the volumes between the double walls of each sheet containing the first high thermal capacity material 11.

FIGS. 4–6 show another embodiment of the invention in which the entire device may be turned inside out like a reversible jacket, As shown in the first mode of operation in FIG. 4, the device 1 is formed of two double walled sheets 3, 4 containing in the volumes 10 between outer panels 9 and inner panels 8 a first high thermal capacity material 11. The two sheets are sealed on three edges and not sealed on edge 6. The space between the two sheets is divided into three compartments by two webs 14. Each web 14 is sealed on all its edges to one or the other inner panel 8 to define therebetween a sealed compartment 15 containing therein the second high thermal capacity material 12. The third compartment 16 defined by the two webs 14 is open at the edge 6, and is empty.

As shown in FIGS. 5 and 6, the envelope 2 may be everted or turned inside out to the configuration of FIG. 6 in which the second material 12 is on the outside enveloping the first material 11 on the inside. This embodiment may be useful when the different physical properties of materials 11 and 12 may be more useful on the outside for certain applications, making a single device more versatile.

Referring now to FIGS. 8 and 9, the heating or cooling pad or heat transfer device 30 of the invention comprises a flexible outer envelope 42 that can conform to a body part when applied thereto and secured with elongate straps that terminate in hook 44 and loop 45 fasteners. Other fasteners such as snaps, buckles and the like may be used. The envelope 42 is formed of a first sheet or panel 46 and a second sheet or panel 47 that are heat sealed together along all edges 48 to enclose a volume 49. Enclosed within volume 49 is a high thermal capacity first material 53 being, for example, one of the freezing gels well known in the art, such as that disclosed by U.S. Pat. No. 4,324,111 which changes state from liquid to slush at around zero degrees centigrade and requires considerable heat energy as it warms through this change of state to serve as an artificial ice that is not rigid. U.S. Pat. No. 5,314,005 discusses other materials for this purpose including some that may be heated in a microwave oven for use as hot packs.

The envelope is comprised of flexible sheet that is impermeable to first material and is readily conformable to the body part when strapped thereto for effective contact and heat transfer.

The thickness of the various sheet materials has been exaggerated for illustrative purposes enclosed within the volume 49, and surrounded by first material 53, is a flexible inner pouch 60. The pouch 60 encloses an inner space 62 that is filled with a high thermal capacity second material 55. The webs 61 and 63 from which the pouch 60 its formed is a flexible sheet such as a plastic heat sealable film that is impervious to the first and second materials so that they cannot mix. The pouch 60 is formed by heat sealing all the edges 66 of two webs 61 and 63 of the plastic film.

Figure 10:
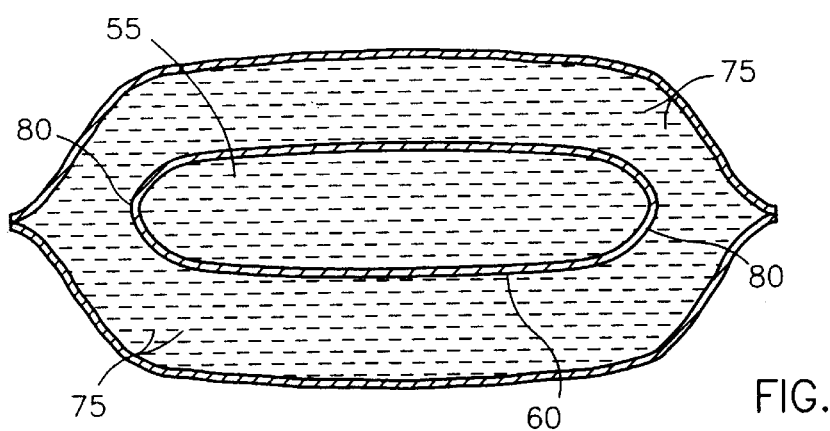
FIG. 10 is a sectional view of yet another embodiment of the invention.

Referring now to FIG. 10, another embodiment is shown in which the inner pouch 60 is formed from an extruded plastic film having opposed rounded edges 80. A length of the extruded tube is sealed at one end, filled with second material 55 and then sealed at a second end. At least one of the inner pouch space or the surrounding outer volume may be provided with elongate strips or fibers 75 to slow heat transfer by reducing convective movement.

The high thermal capacity material 55 in the pouch 60 may be identical to, or different than, the material 53 within the envelope walls. It may even be rigid when frozen such as plain water, since segmentation provides some flexibility.

The materials 55 and 53 may be selected on the basis of their particular physical properties to enhance the utility of the device. Those properties include, but are not limited to, heat of fusion, heat capacity, thermal conductivity, temperature of transition from liquid to solid, rigidity in the solid phase, reaction to microwave radiation, vapor pressure and boiling point.

Thermal conductivity of the material 53 is important in the rate of transfer of heat to or from the insert or pouch 60. By acting as a partial insulator, it can prolong the cooling effect and also prevent a very cold or hot inset from injuring the skin, while maintaining a relatively uniform surface temperature.

Figure 11:
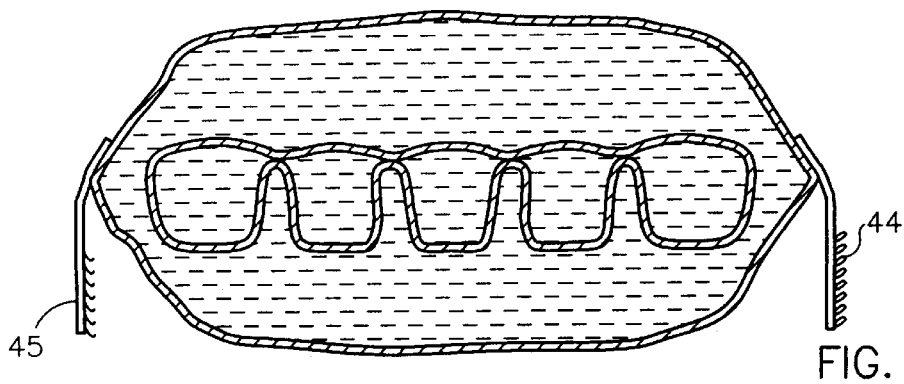
FIG. 11 is a sectional view of still another embodiment of the invention.

Referring now to FIG. 11, another embodiment of an inner pouch 90 is shown in which the pouch is segmented as shown to make it more flexible and to maintain a flatter shape by sealing together along seams 97 the outer walls of the pouch, Referring now to FIGS. 12 and 13, another embodiment is shown in which there are a plurality of inner pouches 120 that are not attached to each other that are contained within the outer envelope 102. Each pouch 120 defines a volume 123 which contains high thermal capacity second material 55 and the pouches are surrounded by high thermal capacity first material 53.

Although discussed primarily for treatment of the body, the device of the invention may be used for heating or cooling any surface.

Instant hot or cold disposable packs are well known in the art. They are devices that consist of a sealed plastic bag containing separated chemicals such as, for example, a dry chemical with either a positive or a negative heat of solution and a sealed plastic bag of water. The device is activated by bursting the separating partition or inner bag of water and mixing the two ingredients to produce instant heat or cold. In an alternative embodiment of the invention shown in FIG. 14, the inner pouch 140 may be one of these instant hot or cold packs.

In this embodiment, water 141 is contained in a first chamber 149 hermetically sealed from second chamber 151 by frangible partition 154. Second chamber 151 contains crystals that get hot or cold when dissolved in water. When the outer envelope 42 is squeezed to cause frangible partition 154 to burst, water dissolves the crystals an produces heat or cold.

The above disclosed invention has a number of particular features which should preferably be employed in combination although each is useful separately without departure from the scope of the invention. While I have shown and described the preferred embodiments of my invention, it will be understood that the invention may be embodied otherwise than as herein specifically illustrated or described, and that certain changes in the form and arrangement of parts and the specific manner of practicing the invention may be made within the underlying idea or principles of the invention.

I claim:

1. A heating or cooling pad comprising:
    A) an outer, flexible, sealed, envelope containing a high thermal capacity first material, said envelope being impervious to said first material;
    B) at least one inner pouch also contained within said envelope, said pouch comprising a high thermal capacity second material sealed within an enclosing web that is impervious to said second material, so that said first and second materials cannot mix;
    C) means associated with said outer envelope and inner pouch for retaining said inner pouch in position relative to said outer envelope.

2. The heating or cooling pad according to claim 1, in which said first material is non-rigid at about zero degrees centigrade.

3. The heating or cooling pad according to claim 2, in which said first and second materials have different physical properties.

4. The heating or cooling pad according to claim 1, in which said first and second materials have different physical properties.

5. The heating or cooling pad according to claim 1, in which said at least one inner pouch is segmented.

6. The heating or cooling pad according to claim 1, in which said enclosing web is formed of a flexible extruded web having two opposed rounded edges.

7. The heating or cooling pad according to claim 1, in which elongate fibers are provided within at least one of said first and second material.

8. The heating or cooling pad of claim 1, wherein said means associated with said outer envelope and inner pouch includes at least one transverse web connected between opposed sides of said outer envelope and cooperating with at least one corresponding notch defined by said inner pouch to retain said pouch in substantially fixed relationship within said envelope.

9. The heating or cooling pad of claim 1, wherein said means associated with said outer envelope and inner pouch is a fixed connection between said pouch and said envelope wherein said pouch is fused to said outer envelope.

10. The heating or cooling pad described in claim 1, wherein said first material is non-rigid at about zero degrees centigrade.

11. A heat transfer device for heating and cooling a surface, the device comprising:
    an envelope formed of first and second sheets, the sheet having broad faces;

each sheet formed of an outer panel of flexible, liquid-impermeable webbing, the panels joined together on all edges to define therebetween a volume that contains a high thermal capacity first material; and the volume further containing therein at least one pouch sealingly enclosing a space, the space containing therein a high thermal capacity second material, the pouch being formed of web that is impermeable to said first and second material so that said first and second materials cannot mix;

means connecting said pouch to said envelope so that said pouch is substantially fixed relative to said envelope.

12. The device according to claim 11, in which said first and second material have different physical properties.

13. The device according to claim 11, in which said at least one pouch is segmented.

14. The device according to claim 11, in which said first and second material have the same physical properties.

15. The device according to claim 11, in which said first material is a freezing gel.

16. The device according to claim 11, in which elongate fibers or strips are provided in one or both of the space and the volume.

17. The heat transfer device of claim 11, wherein said means connecting said pouch to said envelope includes at least one web connected at one side to said envelope and at another side to said pouch.

18. The heating or cooling pad as described in claim 11, wherein said first material is not rigid at about zero degrees centigrade.

19. A heating or cooling pad comprising:

A) an outer, flexible, sealed, envelope containing a high thermal capacity first material, said envelope being impervious to said first material;

B) at least one inner pouch also contained within said envelope, said pouch comprising a high thermal capacity second material sealed within an enclosing web that is impervious to said second material, so that said first and second materials cannot mix, in which said at least one inner pouch further comprises two separate chambers hermetically sealed from each other by a frangible partition and the two chambers containing different materials which, when mixed together after manually breaking said partition, form said high thermal capacity second material and also produce either heat or cold upon mixing;

C) said first material being non-rigid at about zero degrees centigrade.

20. A heat transfer device for heating and cooling a surface, the device comprising:

an envelope formed of first and second sheets, the sheet having broad faces;

each sheet formed of an outer panel of flexible, liquid-impermeable webbing, the panels joined together on all edges to define therebetween a volume that contains a high thermal capacity first material that is not rigid at about zero degrees centigrade; and the volume further containing therein at least one pouch sealingly enclosing a space, the space containing therein a high thermal capacity second material, the pouch being formed of web that is impermeable to said first and second material so that said first and second materials cannot mix, in which said at least one pouch further comprises two separate chambers hermetically sealed from one another by a frangible partition and the two chambers contain different parts which, when mixed together after manually rupturing the partition, from said high thermal capacity second material and also generate either heat or cold.

* * * * *